US005753643A

United States Patent [19]

Andersen et al.

[11] Patent Number: 5,753,643
[45] Date of Patent: May 19, 1998

[54] HETEROCYCLIC COMPOUNDS

[75] Inventors: Henrik Sune Andersen, København Ø; Knud Erik Andersen, Smørum; Rolf Hohlweg, Kvistgaard; Peter Madsen, Bagsvaerd; Tine Krogh Jørgensen, Herlev; Uffe Bang Olsen, Vallensbaek, all of Denmark

[73] Assignee: Novo Nordisk A/S, Bagsvaerd, Denmark

[21] Appl. No.: 862,169

[22] Filed: May 22, 1997

Related U.S. Application Data

[62] Division of Ser. No. 625,562, Mar. 28, 1996.

[30] Foreign Application Priority Data

Apr. 7, 1995 [DK] Denmark .................. 0406/96
Sep. 11, 1995 [DK] Denmark .................. 1003/95

[51] Int. Cl.$^6$ .................. C07D 207/12; C07D 211/60; A61K 31/55
[52] U.S. Cl. .................. 514/211; 514/213; 514/215; 514/217; 514/220; 514/319; 514/408; 514/423; 540/545; 540/549; 540/557; 540/576; 540/587; 546/195; 548/528

[58] Field of Search .................. 514/211, 215, 514/217, 220, 213, 319, 408, 423; 540/545, 549, 557, 587, 576; 546/195; 548/528

[56] References Cited

U.S. PATENT DOCUMENTS

| | | | |
|---|---|---|---|
| 3,347,849 | 10/1967 | Schmultz | 260/239 |
| 3,381,000 | 4/1968 | Drukker et al. | 260/239 |
| 3,391,136 | 7/1968 | Berg | 260/239 |
| 3,542,790 | 11/1970 | Weber et al. | 260/293.4 |
| 4,766,114 | 8/1988 | Malen et al. | 514/211 |
| 5,011,833 | 4/1991 | Meli et al. | 514/211 |
| 5,668,129 | 9/1997 | Andersen et al. | 514/183 |

*Primary Examiner*—Mukund J. Shah
*Assistant Examiner*—Deepak R. Rao
*Attorney, Agent, or Firm*—Steve T. Zelson; Elias J. Lambiris

[57] ABSTRACT

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

21 Claims, No Drawings

HETEROCYCLIC COMPOUNDS

CROSS-REFERENCE TO RELATED APPLICATIONS

This application is a divisional of application Ser. No. 08/625,562 filed Mar. 28, 1996 and claims priority under 35 U.S.C. 119 of Danish application serial nos. 0406/95 and 1003/95 filed Apr. 7, 1995 and Sep. 11, 1995, respectively, the contents of which are fully incorporated herein by reference.

FIELD OF THE INVENTION

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophelitis, glaucoma, gastrointestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1-E10, 1993). This peptide may represent an important physiological modulator of intracellular glucose trafficking in physiological conditions, such as exercise, and may also contribute to the decreased insulin action and skeletal muscle glycogen, synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. Nos. 4,383,999 and 4,514,414 and in EP 236342 as well as in EP 231996 some derivatives of N-(4,4-disubstituted-3-butenyl)-azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

DESCRIPTION OF THE INVENTION

The present invention relates to novel N-substituted azaheterocyclic carboxylic acids and esters thereof of formula I

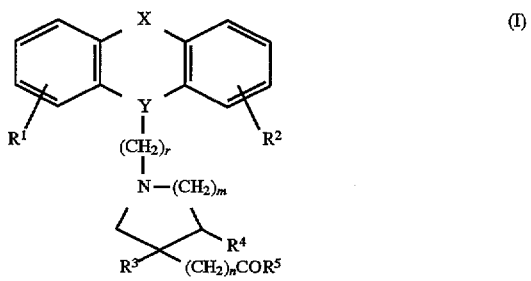

wherein $R^1$ and $R^2$ independently are hydrogen, halogen, trifluoromethyl, hydroxy, $C_{1-6}$-alkyl or $C_{1-6}$-alkoxy; and Y is >N—CH$_2$—, >CH—CH$_2$— or >C=CH— wherein only the underscored atom participates in the ring system; and X is ortho phenylene, —CH$_2$—(C=O)—, —(C=O)—CH$_2$,—CH$_2$—S—, —S—CH$_2$—, —CH$_2$—N(R$^8$)—, —N(R$^8$)—CH$_2$—, —N(CH$_3$)—SO$_2$—, —SO$_2$—N(CH$_3$)—, —CH(R$^7$)—CH$_2$— or —CH$_2$—CH(R$^7$)— wherein R$^8$ is hydrogen or $C_{1-6}$-alkyl and R$^7$ is $C_{1-6}$— alkyl or phenyl; and r is 1,2 or 3; and m is 1 or 2; and n is 1 when m is 1 and n is 0 when m is 2; and $R^3$ and $R^4$ each represents hydrogen or may—when m is 2—together represent a bond; and $R^5$ is —OH or $C_{1-6}$—alkoxy;

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

1-(3-(9H-Tribenz[b,d,f]azepin-9-yl)-1-propyl)-3-piperidinecarboxylic acid;

1-(3-(Tribenzo[a,c,e]cyclohepten-9-ylidene)-1 -propyl)-3-piperidinecarboxylic acid;

1-(3-(5-Methyl-5,6-dihydrodibenz[b,e]azepin-11-ylidene)-1-propyl)-3-5piperidinecarboxylic acid;

1-(3-(6-Methyl-6H-dibenzo[c,f][1,2]thiazepin-5,5-dioxide-11-ylidene)-1-propyl)-3-piperidinecarboxylic acid;

1-(3-(10-Methyl-10,11-dihydro-5H-dibenzo[b,e]cyclohepten-5-ylidene)-1-propyl)-3-piperidinecarboxylic acid;

1-(3-(10-Phenyl-10,11-dihydro-5H-dibenzo[b,e]cyclohepten-5-ylidene)-1-propyl)-3-piperidinecarboxylic acid;

1-(3-(6,11-Dihydro-11H-dibenzo[b,e][1,4]thiazepin-11-yl)-1-propyl)-3-piperidinecarboxylic acid;

1-(3-(10-Methyl-10,11-dihydro-dibenzo[b,e][1,4]diazepin-5-yl)-1-propyl)-3-piperidinecarboxylic acid;

(R)-1-(3-(10-Oxo-10,11-dihydro-5H-dibenz[b,f]azepin-5-yl)-1-propyl)-3-piperidinecarboxylic acid;

(R)-1-(3-(6-Methyl-6,11-dihydro-dibenzo[c,f][1,2,5]thiadiazepin-5,5-dioxide-11-yl)-1-propyl)-3-piperidinecarboxylic acid;

(R)1-(3-(6,11-Dihydro-dibenz[b,e]thiepin-11-yl)-1-propyl)-3-piperidinecarboxylic acid;

(R)-1-(3-(5-Methyl-5,6-dihydrodibenz[b,e]azepin-11-ylidene)-1-propyl)-3-piperidinecarboxylic acid;

(R)-1-(3-(9H-Tribenzo[a,c,e]cyclohepten-9-ylidene)-1-propyl)-3-piperidinecarboxylic acid;

(R)-1-(3-(9H-Tribenz[b,d,f]azepine-9-yl)propyl)-3-piperidinecarboxylic acid;

or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.: Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

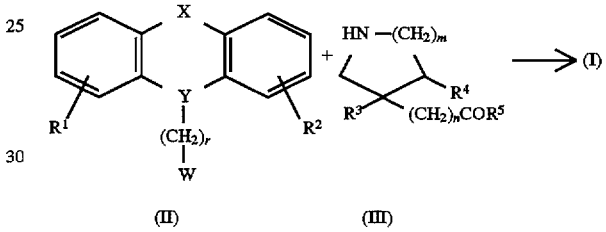

A compound of formula II wherein $RK^1$, $R^2$, X, Y and r are as defined above and W is a suitable leaving group such as halogen, p-toluene sulphonate or mesylate may be reacted with an azaheterocyclic compound of formula III wherein $R^3$, $R^4$, $R^5$, m and n are as defined above. This alkylation reaction may be carried out in a solvent such as acetone, dibutylether, 2-butanone, methyl ethyl ketone, ethyl acetate, tetrahydrofuran (THF) or toluene in the presence of a base e.g. potassium carbonate and a catalyst, e.g. an alkali metal iodide at a temperature up to reflux temperature for the solvent used for e.g. 1 to 120 h. If esters have been prepared in which $R^5$ is alkoxy, compounds of formula I wherein $R^5$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 ml 1 % formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Reduced release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of formalin induced pain response for some representative compounds are recorded in table 1.

TABLE 1

Inhibition of formalin induced pain response at 0.1 mg/kg

| Example no. | % Pain inhibition |
| --- | --- |
| 1 | 21 |
| 3 | 31 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax. If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | | |
| --- | --- | --- |
| Active compound (as free compound or salt thereof) | | 100 mg |
| Colloidal silicon dioxide (Areosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | |
| Coating: | | |
| HPMC | approx. | 9 mg |
| *Mywacett ® 9–40 T | approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography, CDCl$_3$ is deuterio chloroform and DMSO-d$_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

EXAMPLE 1

(R)-1-(3-(10-Oxo-10,11-dihydro-5H-dibenz[b,f]azepin-5-yl)-1-propyl)-3-piperidinecarboxylic acid hydrochloride

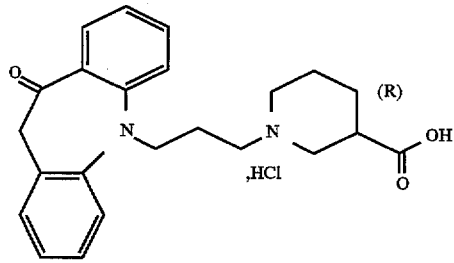

To a solution of 10-methoxy-5H-dibenz[b,f]azepine (2.0 g, 9.0 mmol, prepared as described in Swiss Patent 389,619)

in dry tetrahydrofuran (50 ml) kept under an atmosphere of nitrogen, n-butyl lithium (3.5 ml, 9.4 mmol, 2.7M in n-hexane) was added dropwise at −40° C. and the reaction mixture was stirred at −40 C. for 0.5 hour. 1-Bromo-3-chloropropane (1.6 g, 9.9 mmol), dissolved in dry tetrahydrofuran (10 ml) was added dropwise at −45° C. and the reaction mixture was stirred at room temperature for 18 hours. n-Butyl lithium (1.0 ml, 2.7 mmol, 2.7M in n-hexane) was added dropwise at 0° C. and the reaction mixture was stirred at 0° C. for 0.5 hour. 1-Bromo-3-chloropropane (0.5 g, 3.1 mmol) dissolved in dry tetrahydrofuran (1 ml) was added dropwise at 0° C. and the reaction mixture was stirred at room temperature for 2 hours. n-Butyl lithium (2.5 ml, 5.4 mmol, 2.7M in n-hexane) was added dropwise at 0° C. and the reaction mixture was stirred at room temperature for 18 hours. The reaction mixture was quenched with water (50 ml) and extracted with diethyl ether (50 ml). The organic extract was washed with brine (40 ml) and dried (MgSO$_4$), filtered and the solvent was evaporated in vacuo. Yield 2.9 g of crude 1-chloro-3-(10-methoxy-10,11-dihydro-5H-dibenz[b,f]azepin-5-yl)propane.

A mixture of the above chloride (2.5 g, 8.3 mmol), (R)-3-piperidinecarboxylic acid ethyl ester tartrate (5.1 g, 16.6 mmol), dry potassium carbonate (6.9 g, 49.7 mmol), potassium iodide (2.8 g, 16.6 mmol) and methyl ethyl ketone (100 ml) was heated at reflux temperature for 66 hours under an atmosphere of nitrogen. The cooled reaction mixture was quenched with water (100 ml) and extracted with diethyl ether (100 ml). The organic extract was extracted with 1N hydrochloric acid (2×100 ml). The combined aqueous extracts were washed with diethyl ether (100 ml), basified with 5N sodium hydroxide to pH=10 and extracted with diethyl ether (2×100 ml). The combined organic extracts were washed with brine (80 ml), dried (MgSO$_4$), filtered and the solvent was evaporated in vacuo. The crude product (2.0 g) was purified by column chromatography on silica gel (600 ml) using a mixture of ethyl acetate, heptane and triethylamine (10:20:0.01) as eluent. This afforded 0.6 g (18 %) of (R)-1-(3-(10-oxo-10,11-dihydro-5H-dibenz[b,f]azepin-5-yl)-1-propyl)-3-piperidinecarboxylic acid ethyl ester as an oil.

TLC: $R_f$=0.24 (SiO$_2$: ethyl acetate/heptane/triethylamine=10:20:0.04).

To a mixture of the above ethyl ester (0.5 g, 1.2 mmol) in ethanol (20 ml) and water (10 ml), sodium hydroxide (0.06 g, 1.5 mmol) was added and the reaction mixture was stirred for 18 hours at room temperature. The solvent was evaporated in vacuo and water (100 ml) was added. The aqueous mixture was washed with diethyl ether (2×100 ml), acidified with 2N hydrochloric acid and washed with dichloromethane (3×200 ml). The aqueous phase was evaporated in vacuo and the residue was suspended in dichloromethane (100 ml) and stirred for 1 hour at room temperature. The mixture was filtered. The filtrate was evaporated in vacuo and the residue was resuspended in diethyl ether (10 ml). The solid was filtered off, washed with diethyl ether and dried in vacuo at 50° C. overnight. This afforded 0.1 g (18%) of the title compound as an amorphous powder.

Calculated for C$_{23}$H$_{26}$N$_2$O$_3$, HCl, 1.75 H$_2$O: C, 61.88%; H, 6.89%; N, 6.27%; Found: C, 61.83%; H, 6.59%; N, 5.94%.

EXAMPLE 2

(R)-1-(3-(6-Methyl-6,11-dihydro-dibenzo[c,f][1,2,5]thiadiazepin-5,5-dioxide-11-yl)-1-propyl)-3-piperidinecarboxylic acid hydrochloride

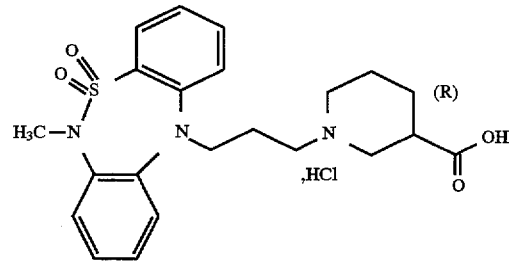

To a solution of 6-methyl-6,11-dihydro-dibenzo[c,f][1,2,5]thiadiazepine-5,5-dioxide (6.51 g, 0.025 mol, prepared as described in J. Med. Chem. 34, 1356 (1991)) in dry tetrahydrofuran (60 ml) kept under an atmosphere of nitrogen, n-butyl lithium (10.37 ml, 0.028 mol, 2.7 M in n-hexane) was added dropwise at −50° C. When the addition was complete the reaction mixture was stirred at −50° C. for 0.5 hour. A solution of 2-(3-bromo-1-propyloxy)tetrahydro-2H-pyran (6.25 g, 0.028 mol) in dry tetrahydrofuran (10 ml) was added dropwise at −40° C. and the reaction mixture was stirred at 50° C. for 20 hours. An additional portion of 2-(3-bromo-1-propyloxy)tetrahydro-2H-pyran (3.13 g, 0.014 mol) dissolved in dry tetrahydrofurane (1 ml) was added at 50° C. and the reaction mixture was stirred at 50° C. for additionally 20 hours. The reaction mixture was quenched with saturated ammonium chloride (50 ml) and extracted with ethyl acetate (2×200 ml). The combined organic extracts were washed with water (2×100 ml) and dried (Na$_2$SO$_4$), filtered and the solvent was evaporated in vacuo. The residue was dissolved in dichloromethane (20 ml) and filtered. The filtrated was evaporated in vacuo and the residue crude product was purified by column chromatography on silica gel (800 ml) using dichloromethane as eluent and later on ethyl acetate as eluent. This afforded 4.1 g (42%) of 11-(3-(tetrahydro-2H-pyran-2-yloxy)-1-propyl)-6-methyl-6,11-dihydro-dibenzo[c,f][1,2,5]thiadiazepin-5,5-dioxide.

TLC: $R_f$=0.19 (SiO$_2$: dichloromethane).

To a solution of 11-(3-(tetrahydro-2H-pyran-2-yloxy)-1-propyl)-6-methyl-6,11-dihydro-dibenzo[c,f]-[1,2,5]thiadiazepin-5,5-dioxide (4.0 g, 10.3 mmol) in dry methanol (50 ml), p-toluenesulphonic acid (0.98 g, 5.1 mmol) was added and the reaction mixture was stirred at room temperature for 60 hours followed by heating at reflux for 1 hour. The solvent was evaporated in vacuo and the residue dissolved in ethyl acetate (100 ml), washed with water (3×50 ml), dried (Na$_2$SO$_4$), filtered and the solvent evaporated in vacuo. This afforded 3.0 g (92%) of 11-(3-hydroxy-1-propyl)-6-methyl-6,11-dihydro-dibenzo-[c,f]-[1,2,5]thiadiazepin-5,5-dioxide as an oil.

TLC: $R_f$=0.31 (SiO$_2$: dichloromethane/ethyl acetate 9:1).

To a solution of 11-(3-hydroxy-1-propyl)-6-methyl-6,11-dihydro-dibenzo-[c,f][1,2,5]thiadiazepin-5,5-dioxide (2.99 g, 9.4 mmol) in dry tetrahydrofuran (30 ml) and triethylamine (4 ml), methanesulfonyl chloride (0.92 ml, 11.74 mmol) dissolved in dry tetrahydrofuran (10 ml) was added dropwise at −5° C. The reaction mixture was stirred at room temperature for 20 hours, quenched with water (100 ml) and extracted with ethyl acetate (2×50 ml). The combined organic extracts were washed with brine (50 ml), dried (Na$_2$SO$_4$), filtered and evaporated in vacuo. This afforded methanesulfonic acid 3-(6-methyl-6,11-dihydro-dibenzo[c,f][1,2,5]thiadiazepin-5,5-dioxo-11-yl)-1-propyl ester in quantitative yield as an oil.

TLC: $R_f$=0.61 (SiO$_2$: heptane/ethyl acetate=1:4).

A mixture of the above methanesulfonate (3.12 g, 9.4 mmol), (R)-3-piperidinecarboxylic acid ethyl ester tartrate (3.75 g, 12.21 mmol), dry potassium carbonate (7.87 g, 56.4 mmol), and methyl ethyl ketone (80 ml) was heated at reflux temperature for 18 hours under an atmosphere of nitrogen. The cooled reaction mixture was filtered and the filter cake washed with ethyl acetate (100 ml). The filtrate was evaporated In vacuo. The crude product (4.85 g) was purified by column chromatography on silica gel (500 ml) using ethyl acetate as eluent. This afforded 1.91 g (46%) of (R)-1-(3-(6-methyl-6,11-dihydro-dibenzo[c,f][1,2,5]thiadiazepin-5,5-dioxo-11-yl)-1-propyl)-3-piperidinecarboxylic acid ethyl ester as an oil.

TLC: $R_f$=0.28 (SiO$_2$: ethyl acetate).

HPLC retention time =17.41 min. (water/acetonitril 7:3, 0.01N (NH$_4$)$_2$SO$_4$ buffer pH=3, flow=1 ml/min, C-18 $R_f$ column)

The above ethyl ester (1.43 g, 3.14 mmol) was dissolved in a mixture of ethanol (13 ml) and water (13 ml). Sodium hydroxide (0.16 g, 3.9 mmol) was added and the reaction mixture was stirred for 18 hours at room temperature. An additional portion of sodium hydroxide (0.13 g, 3.14 mmol) was added and the reaction mixture stirred for an additional 4 hours at room temperature. The solvent was evaporated in vacuo, water (15 ml) and brine (15 ml) were added. The aqueous mixture was washed with dichloromethane (2×15 ml), diethyl ether (30 ml) and acidified with concentrated hydrochloric acid. The precipitate was separated and dissolved in water (50 ml). The resulting mixture was washed with dichloromethane (2×50 ml) and diethyl ether (2×50 ml). The aqueous phase was evaporated in vacuo and the residue was suspended in 2-propanol (100 ml), stirred 0.5 hour at room temperature and filtered. The filtrate was evaporated in vacuo and triturated with diethyl ether (50 ml), filtered off, and washed with diethyl ether. The filtercake (0.93 g) was stirred with 2-propanol (15 ml) for 2 hours, the precipitate filtered off and washed with 2-propanol. The organic phase was evaporated in vacuo and the residue dissolved in ethanol and precipitated with diethyl ether, filtered off and washed with diethyl ether and dried in vacuo at 50° C. This afforded 0.31 g (21%) of the title compound as an amorphous powder.

HPLC retention time=7.08 min. (water/acetonitril 7:3, 0.01N (NH$_4$)$_2$SO$_4$ buffer pH=2.5, flow=1 ml/min, C-18 $R_f$ column)

$^1$H NMR (200 MHz, DMSO-d$_6$) $\delta_H$ 1.46 (bs, 1H), 1.79 (bs, 1H), 1.96 (bs, 4H), 2.67–3.03 (m, 3H), 3.11 (bt, 2H), 3.19–3.54 (m, 4H), 3.95 (bt, 2H), 4.35 (bs, 1H), 7.13 (t, 1H), 7.25 (m, 1H), 7.43 (m, 4H), 7.52 (m, 1H), 7.68 (dd, 1H). Calculated for C22H$_{27}$N$_3$O$_4$S, HCl, 1.5 H$_2$O: C, 53.60%; H, 6.34%; N, 8.52%; Found: C, 53.75%; H, 6.41%; N, 8.14%.

EXAMPLE 3

(R)-1-(3-(6,11-Dihydro-dibenz[b,e]thiepin-11-yl)-1-propyl)-3-piperidinecarboxylic acid hydrochloride

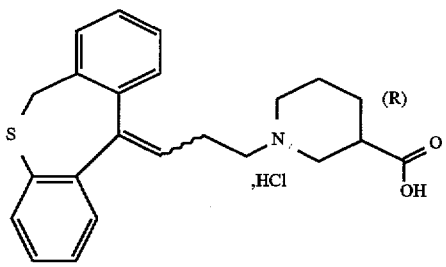

A solution of cyclopropylmagnesium bromide in dry tetrahydrofuran (prepared from cyclopropyl bromide (3.7 g, 0.031 mol), magnesium turnings (0.8 g, 0.033 mol) and dry tetrahydrofuran (50 ml) under an atmosphere of nitrogen) was added dropwise to a solution of (6,11-dihydro-dibenz-[b,e]thiepin-11-one (3.5 g, 0.016 mol, prepared as described in Chem. Pharm. Bull. 39, 1991, 2564) in dry tetrahydrofuran (50 ml). When addition was complete the mixture was heated at 50° C. for 2 hours. The reaction mixture was cooled on an ice-bath and saturated ammonium chloride (50 ml) and water (50 ml) were carefully added. The mixture was extracted with diethyl ether (2×100 ml), dried (MgSO$_4$), filtered and the solvent was evaporated in vacuo to give 4.4 g of crude 11-cyclopropyl-6,11-dihydro-11H-dibenzo[b,e]thiepin-11-ol as an oil.

The above crude alcohol (4.0 g) was dissolved in dichloromethane (50 ml) and a solution of trimethylsilyl bromide (2.1 ml, 0.016 mol) was added dropwise at room temperature. When addition was complete the mixture was stirred at room temperature for 1.5 hour and water (50 ml) was added. The phases were separated and the organic phase was washed with water (50 ml), dried (MgSO$_4$) and the solvent was evaporated in vacuo to give 4.1 g (83%) of crude 1-bromo-3-(6,11-dihydro-dibenzo[b,e]thiepin-11-ylidene)-propane as a solid.

A mixture of the above crude bromide (1.0 g, 3.02 mmol), (R)-3-piperidinecarboxylic acid ethyl ester tartrate (1.9 g, 6.04 mmol), potassium carbonate (2.5 g, 18.11 mmol), potassium iodide (1.0 g, 6.02 mmol) and methyl ethyl ketone (100 ml) was heated at reflux temperature for 18 hours. The cooled reaction mixture was quenched with water (100 ml) and extracted with diethyl ether (2×100 ml). The combined organic extracts were extracted with 5N hydrochloric acid (2×100 ml) and the aqueous phase washed with diethyl ether (50 ml). The aqueous phase was basified with 50% sodium hydroxide and extracted with diethyl ether (2×100 ml). The combined organic extracts were washed with saturated ammonium chloride (100 ml), dried (MgSO$_4$), filtered and the solvent evaporated in vacuo. This afforded 0.50 g (41 %) of (R)-1-(3-(6,11-dihydro-dibenz[b,e]thiepin-11-yl)-1-propyl)-3-piperidine-carboxylic acid ethyl ester as an oil.

TLC: $R_f$=0.44 (SiO$_2$: ethyl acetate/heptane=1:1)

The above ethyl ester (0.5 g, 1.23 mmol) was dissolved in ethanol (10 ml) and a solution of sodium hydroxide (60 mg, 1.47 mmol) in water (5 ml) was added. The reaction mixture was stirred for 18 hours at room temperature and the solvent was removed in vacuo. Water (75 ml) was added and the mixture was washed with diethyl ether (2×50 ml). The aqueous phase was acidified (pH=1) with concentrated hydrochloric acid and extracted with dichloromethane (3×50 ml). The combined organic extracts were washed with water (50 ml), dried (MgSO$_4$), filtered and the solvent evaporated in vacuo. The residue was suspended in a mixture of acetone (5 ml) and diethyl ether (10 ml) and stirred for 18 hours at room temperature. The precipitate was filtered off, washed with diethyl ether and dried in vacuo at 50° C., to give 0.15 g (29 %) of the title compound as an amorphous solid.

Calculated for C$_{21}$H$_{25}$NO$_2$S, HCl: C, 66.41%; H, 6.30%; N, 3.37%; Found: C, 66.63%; H, 6.57%; N, 3.54%.

EXAMPLE 4

(R)-1 -(3-(5-Methyl-5,6-dihydrodibenz[b,e]azepin-1 1-ylidene)-1 -propyl)-3-.piperidinecarboxylic acid dihydrochloride

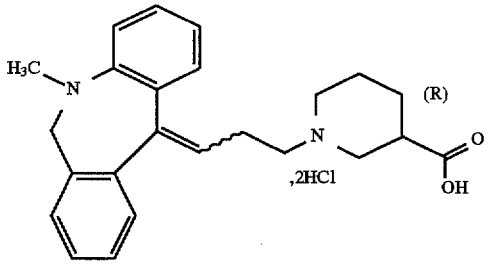

To a mixture of 5H-dibenz[b,e]azepine-6,11-dione (5.0 g, 22.4 mmol), ethylene glycol (12.5 ml, 0.224 mol) and nitromethane (60 ml) in dry toluene (100 ml) kept under an atmosphere of nitrogen, triflic acid (0.4 ml, 4.48 mmol) was added dropwise. The reaction mixture was heated at reflux temperature for 3 days with a water separator. The cooled reaction mixture was quenched with water (100 ml) and extracted with ethyl acetate (80 ml). The organic extract was washed with water (3×80 ml) and dried (MgSO$_4$), filtered and the solvent evaporated in vacuo. This afforded 5.16 g (86%) of 5H-dibenz[b,e]azepine-6, 11 -dione 11-ethylene ketal as a solid.

TLC: R$_f$=0.32 (SiO$_2$: heptane/ethyl acetate=1:1).

$^1$H NMR (200 MHz, DMSO-d$_6$) $\delta_H$ 3.75 (m, 2H), 4.17 (t, 2H), 7.06–7.80 (m, 8H), 10.58 (s, 1H).

To a solution of the above ketal (35.7 g, 0.134 mol) in dry N,N-dimethylformamide (250 ml) kept under an atmosphere of nitrogen, sodium hydride (6.4 g, 0.160 mol, 60 % dispersion in mineral oil) was added in portions and the reaction mixture was stirred for 0.5 hour. A solution of iodomethane (22.7 g, 0.160 mol) in N,N-dimethylformamide (50 ml) was slowly added dropwise maintaining the temperature below 30° C. by external cooling. When the addition was complete the mixture was stirred for 1.5 hour. The solution was poured onto a mixture of water (50 ml) and saturated ammonium chloride (100 ml). The precipitate was filtered off and washed with water (500 ml), heptane (400 ml) and dried in vacuo at 50° C. This afforded 35.1 g (93%) of 5-methyl-5H-dibenz[b,e]azepin-6,11-dione-11-ethylene ketal as a solid.

M.p. 192°–192.60° C.

$^1$H NMR (200 MHz, DMSO-d$_6$) $\delta_H$ 3.51 (s, 3H), 3.73–3.94 (m, 2H), 4.10–4.27 (m, 2H), 7.18 (dt, 1H), 7.34–7.61 (m, 6H), 7.68 (dd, 1H).

In a dry, 1 L three-necked flask equipped with reflux condenser and thermometer, lithium aluminumhydride (4.2 g, 0.112 mol) was suspended in dry diethyl ether (200 ml) under a nitrogen atmosphere. Cautiously, a solution of 5-methyl-5H-dibenz[b,e]azepin-6,11-dione-11-ethylene ketal (30.0 g, 0.11 mol) in dry tetrahydrofuran (250 ml) was added dropwise. The mixture was heated at reflux temperature for 1.5 hour, cooled to room temperature and quenched by cautious addition of water (4 ml) and 25% sodium hydroxide (4 ml), MgSO$_4$ and filtered. The filtrate was evaporated until dryness affording 31 g which was purified by column chromatography on silica gel (1000 ml) using a mixture of heptane and ethyl acetate (3:1) as eluent. This afforded 13 g (46 %) of 5-methyl-5,6-dihydro-5H-dibenz[b,e]azepin-11-one ethylene ketal as an oil.

TLC: R$_f$=0.63 (SiO$_2$: heptane/ethyl acetate=2:1).

The above ketal (13 g, 0.063 mol) was dissolved in 85% ethanol (100 ml) and concentrated hydrochloric acid (8 ml) was added and the reaction mixture was heated at reflux for 2 hour. The solvent was evaporated and water (100 ml) was added to the residue and the mixture was extracted with ethyl acetate (2×100 ml). The combined organic extracts were washed with water (2×100 ml) and brine (100 ml), dried (MgSO$_4$) and filtered and the solvent evaporated in vacuo. The residue (10.1 g) was washed with heptane (30 ml), filtered and the filter cake washed with heptane (30 ml) and dried. This afforded 9.0 g (83 %) of 5-methyl-5,6-dihydro-5H-dibenz[b,e]azepin-1 1-one as a solid compound. M.p. 101°–104° C.

$^1$H NMR (200 MHz, CDCl$_3$) $\delta_H$ 3.23 (s, 3H), 4.24 (s, 2H), 6.83 (m, 2H), 7.22 (dd, 1H), 7.18 (dt, 1H), 7.20–7.51 (m, 3H), 7.74 (dd, 1H), 8.29 (dd, 1H).

A solution of cyclopropylmagnesium bromide in dry tetrahydrofuran (prepared from cyclopropyl bromide (4.7 g, 0.04 mol), magnesium turnings (0.9 g, 0.04 mol) and dry tetrahydrofuran (50 ml) under an atmosphere of nitrogen) was added dropwise to a solution of 5-methyl-5,6-dihydro-5H-dibenz[b,e]azepin-11-one (4.3 g, 0.02 mol) in dry tetrahydrofuran (50 ml). When addition was complete the mixture was heated at reflux temperature for 18 hours. The reaction mixture was cooled on an ice-bath and saturated ammonium chloride (25 ml) and water (100 ml) were carefully added and the resulting mixture extracted with diethyl ether (100 ml). The organic extract was washed with water (100 ml), saturated ammonium chloride (100 ml); dried (MgSO$_4$), filtered and the solvent was evaporated in vacuo to give 5.1 g of crude 11-cyclopropyl-5-methyl-5,6-dihydro-5H-dibenz[b,e]azepin-11-ol as a solid.

The above crude alcohol (4.9 g) was dissolved in dichloromethane (50 ml) and a solution of trimethylsilyl bromide (2.6 ml, 0.02 mol) in dichloromethane (40 ml) was added dropwise at room temperature. When addition was complete the mixture was stirred at room temperature for 1 hour and water (50 ml) was added. The phases were separated and the organic phase was dried (MgSO$_4$) and the solvent was evaporated in vacuo to give 5.0 g (81 %) of crude 11-(3-bromo-1-propylidene)-5-methyl-5,6-dihydro-dibenz-[b,e]azepine as an oil.

A mixture of the above crude bromide (4.8 g, 0.02 mol), (R)-3-piperidinecarboxylic acid ethyl ester tartrate (9.0 g, 0.03 mol), potassium carbonate (12.1 g, 0.09 mol), potassium iodide (4.9 g, 0.03 mol), and methyl ethyl ketone (150 ml) was heated at reflux temperature for 18 hours. The cooled reaction mixture was quenched with water (100 ml) and extracted with ethyl acetate (2×100 ml). The combined organic extracts were washed with water (100 ml), saturated aqueous ammonium chloride (100 ml), dried (MgSO$_4$), filtered and the solvent evaporated in vacuo. The crude product (6.1 g) was purified by column chromatography on silica gel (600 ml) using a mixture of ethyl acetate and heptane (1:2) as eluent. This afforded 2.7 g (46%) of (R)-1-(3-(5-methyl-5,6-dihydrodibenz[b,e]azepin-11-ylidene)-1-propyl)-3-piperidinecarboxylic acid ethyl ester as an oil.

TLC: R$_{f=0.22}$ (SiO$_2$: ethyl acetate/heptane=1:2)

The above ethyl ester (2.0 g, 4.94 mmol) was dissolved in ethanol (40 ml) and a solution of sodium hydroxide (0.24 g, 5.93 mmol) in water (15 ml) was added. The reaction mixture was stirred for 18 hours at room temperature and the solvent was removed in vacuo. Water (150 ml) was added and the mixture was washed with diethyl ether (2×100 ml). The aqueous phase was acidified (pH=1) with concentrated hydrochloric acid and evaporated in vacuo. The residue was suspended in acetone (20 ml) and filtered. To the filtrate was added diethyl ether (10 ml) and the mixture was stirred for 18 hours at room temperature. The precipitate was filtered off, washed with diethyl ether and dried in vacuo at 50° C., to give 0.80 g (36%) of the title compound as an amorphous solid.

Calculated for $C_{24}H_{26}N_2O_2$, 2HCl, $H_2O$: C, 61.67%; H, 6.90%; N, 5.99%; Found: C, 61.71%; H, 7.28%; N, 5.74%.

EXAMPLE 5

(R)-1l-(3-(9H-Tribenzo[a,c,e]cyclohepten-9-ylidene)-1-propyl)-3-piperidinecarboxylic acid hydrochloride

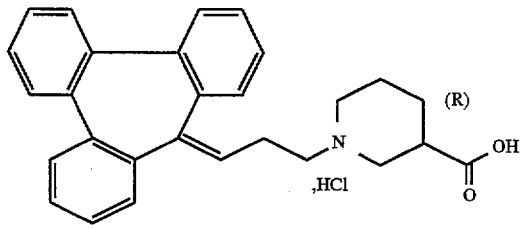

A solution of cyclopropylmagnesium bromide in dry tetrahydrofuran( prepared from cyclopropylbromide (4.54 g, 37.5 mmol), magnesium turnings (0.91 g, 37.5 mmol) and dry tetrahydrofuran (30 ml) ) was placed under an atmosphere of nitrogen. A solution of 9H-tribenzo[a,c,e] cyclohepten-9- one (1.92 g, 7.5 mmol) (prepared according to W. Tochtermann, Chem.Ber., 97, 1329 (1964)) in tetrahydrofuran (20 ml) was added dropwise and when addition was complete the mixture was heated at reflux temperature for 30 minutes. The reaction mixture was cooled on an ice-bath and saturated ammonium chloride (50 ml) was added carefully. The organic layer was separated and the aqueous phase extracted with diethyl ether (2×100 ml). The combined organic extracts were dried (MgSO₄) and the solvent was evaporated in vacuo affording 2.69 g of 9-cyclopropyl-9H-tribenzo[a,c,e]cyclohepten-9-ol.

The above crude alcohol (2.01 g, 6.75 mmol) was dissolved in acetic acid (25 ml) and a 3.7M solution of hydrogen bromide in acetic acid (3.7 ml, 13.5 mmol) diluted with 25 ml acetic acid, was added dropwise. The reaction mixture was stirred for 30 minutes, cooled on an ice-bath and triethylamine (1.9 ml, 13.5 mmol) was added carefully. The mixture was concentrated in vacuo and the remainder was dissolved in toluene (50 ml), washed with saturated sodium hydrogencarbonate (2×50 ml), dried over MgSO₄ and evaporated to furnish 2.9 g of 9-(3-bromo-1-propylidene)-9H-tribenzo[a,c,e]cycloheptene as a solid.

A mixture of the above crude bromide (2.9 g, 6.75 mmol), ethyl (R)-3-piperidine carboxylate tartrate (2.03 g, 6.75 mmol), potassium carbonate (5.6 g, 40.5 mmol), sodium iodide (1.01 g, 6.75 mmol) and 2-butanone (30 ml) was heated at reflux temperature for 3 hours. After cooling to room temperature, diethyl ether (50 ml) and water (50 ml) were added to the reaction mixture. The organic layer was separated, washed with water (2×50 ml) and extracted with 1N hydrochloric acid (20 ml) and water (2×50 ml). The aqueous phase was adjusted to pH 8 with 1N sodium hydroxide solution and extracted with dichloromethane (2×30 ml). The combined organic extracts were dried (MgSO₄) and concentrated in vacuo to furnish 2.0 g of (R)-1-(3-(9H-tribenzo[a,c,e]cycloheptene-9-ylidene)-1-propyl)-3-piperidinecarboxylic acid ethyl ester as an oil.

The above ester (2.0 g, 4.6 mmol) was dissolved in ethanol (25 ml) and 2N sodium hydroxide (7.6 ml) was added and the mixture was stirred at room temperature for 1 hour. The ethanol was evaporated and the remainder was diluted with water (25 ml) pH was adjusted to 1 with 1N hydrochloric acid, the solution was washed with diethyl ether (30 ml) and extracted with dichloromethane (2×30 ml). The combined organic extracts were dried (MgSO₄) and concentrated in vacuo. The remainder was dissolved in a minimum amount of dichloromethane and the product precipitated by addition of diethyl ether (20 ml). Filtration and drying furnished 0.41 g (19%) of the title compound as an amorphous solid.

Calculated for $C_{28}H_{27}NO_2$, HCl, 1.25 $H_2O$: C, 71.78%; H, 6.56%; N, 2.99%; Found: C, 71.68%; H, 6.53%; N, 2.77%.

HPLC retention time=19.12 and 19.43 minutes (mixture of isomers) (5 mm C18 4×250 mm column, eluting with a 20–80% gradient of 0.1% trifluoroacetic acid/acetonitrile and 0.1% trifluoroacetic acid/water over 25 minutes at 35° C.).

EXAMPLE 6

(R)-1-(3-(9H-Tribenz[b,d,f]azepine-9-yl)propyl)-3-piperidinecarboxylic acid, hydrochloride

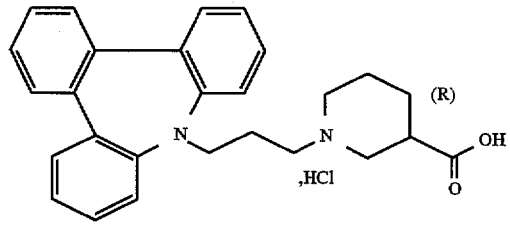

9H-Tribenz[b,d,f]azepine (0.17 g, 0.70 mmol, prepared similarly as described by H. C. Axtell et al., J.Org.Chem. 56, 3906 (1991)) was suspended in dry toluene (5 ml). 3-Chloropropionyl chloride (0.13 g, 1.0 mmol) and triethylamine (0.1 ml) were added and the mixture was heated at reflux temperature for 1.5 hour. Saturated aqueous sodium bicarbonate (10 ml) was added, and the phases were separated. The organic phase was washed with brine (10 ml), dried (MgSO₄) and concentrated in vacuo, affording 220 mg, (94%) of crude 3-chloro-1-(9H-tribenz[b,d,f]azepine-9-yl)propan-1-one as a foam.

A 1M solution of lithium aluminium hydride in tetrahydrofuran (1.32 ml), diluted with dry tetrahydrofuran (5 ml) was cooled on an ice bath and concentrated sulfuric acid (66 mg, 0.66 mmol) was added dropwise. The solution was stirred at room temperature for 0.5 hour. A solution of the above product (0.22 g, 66 mmol) in dry tetrahydrofuran (5 ml) was added dropwise and stirring was continued for 0.5 hour. The reaction was quenched by careful addition of ethyl acetate (1.0 ml) followed by water (0.1 ml). Filtration of the mixture and evaporation of the filtrate in vacuo afforded 210 mg (100%) 9-(3-chloropropyl)-9H-tribenz[b,d,f]azepine as a foam.

A mixture of the above chloride (0.21 g, 0.66 mmol), ethyl (R)-3-piperidinecarboxylate tartrate (0.30 g, 1.0 mmol), potassium carbonate (0.18 g, 2.0 mmol), potassium iodide (0.10 g, 0.60 mmol) and 2-butanone (10 ml) was heated at reflux temperature for 40 hours. After cooling to room temperature, dichloromethane (50 ml) was added and the mixture was filtered. The filtrate was washed with 1N hydrochloric acid (20 ml), water (20 ml) and saturated sodium hydrogencarbonate solution (20 ml), dried over sodium sulfate and evaporated in vacuo. The remainder was dissolved in diethyl ether (20 ml) and a 2.6M solution of hydrogen chloride in diethyl ether (0.5 ml) was added. The formed precipitate was collected by filtration, washed with ether and dried, affording 0.13 g (41%) of (R)-1-(3-(9H-tribenz[b,d,f]azepin-9-yl)propyl)-3-piperidine carboxylic acid ethyl ester hydrochloride as a solid.

The above ester (0.13 g, 0.27 mmol) was dissolved in ethanol (3 ml) and 2N sodium hydroxide (0.6 ml). The mixture was stirred at room temperature for 1.5 hour, acidified by addition of 1N hydrochloric acid (pH 1) and ethanol was removed in vacuo. The aqueous solution was diluted with water (10 ml), washed with diethyl ether (20 ml) and extracted with dichloromethane (30 ml). The organic extract was dried (MgSO$_4$) and concentrated in vacuo to afford 90 mg (74%) of the title compound as a solid HPLC retention time=18.03 minutes (5 mm C18 4=250 mm column, eluting with a 20–80% gradient of 0.1% trifluoroacetic acid/acetonitrile and 0.1% trifluoroacetic acid/water over 25 minutes at 35° C.).
MS(EI) 412 (M$^+$, 19%),

We claim:

1. A compound of formula I

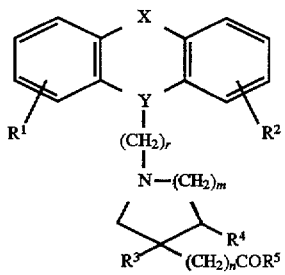

wherein
$R^1$ and $R^2$ independently are hydrogen, halogen, trifluoromethyl, hydroxy, $C_{1-6}$-alkyl or $C_{1-6}$-alkoxy;

Y is >$\underline{N}$—CH$_2$—, >$\underline{C}$H—CH$_2$— or >$\underline{C}$=CH— wherein only the underscored atom participates in the ring system;

X is ortho phenylene, —CH$_2$—N(R$^8$)—, —N(R$^8$)—CH$_2$—, —N(CH$_3$)—SO$_2$—, or —SO$_2$—N(CH$_3$)—, wherein R$^8$ is hydrogen or $C_{1-6}$-alkyl;

r is 1, 2 or 3; and m is 1 or 2; and n is 1 when m is 1 and n is 0 when m is 2;

$R^3$ and $R^4$ each represents hydrogen or may—when m is 2—together represent a bond; and $R^5$ is —OH or $C_{1-6}$-alkoxy; or a pharmaceutically acceptable salt thereof.

2. A compound according to claim 1 wherein $R^1$ and $R^2$ independently represent hydrogen, halogen or $C_{1-6}$-alkoxy.

3. A compound according to claim 2 wherein $R^1$ and $R^2$ independently are hydrogen.

4. A compound according to claim 1 wherein Y is >$\underline{N}$—CH$_2$—.

5. A compound according to claim 1 wherein Y is >$\underline{C}$H—CH$_2$— or >$\underline{C}$=CH—.

6. A compound according to claim 1 wherein X is ortho phenylene.

7. A compound according to claim 1 wherein X is —CH$_2$—N(CH$_3$)— or —N(CH$_3$)—SO$_2$—.

8. A compound according to claim 1 wherein X is —CH$_2$—N(R$^8$)— or —N(R$^8$)—CH$_2$—.

9. A compound according to claim 1 wherein X is —N(CH$_3$)—SO$_2$— or —SO$_2$—N(CH$_3$)—.

10. A compound according to claim 1 wherein r is 2.

11. A compound according to claim 1 wherein m is 2.

12. A compound according to claim 1 wherein $R^3$ and $R^4$ each represents hydrogen.

13. A compound according to claim 1 wherein $R^5$ is —OH.

14. A compound according to claim 1 which is:

(R)-1-(3-(6-Methyl-6,11-dihydro-dibenzo[c,f][1,2,5]thiadiazepin-5,5-dioxide-11-yl)-1-propyl)-3-piperidinecarboxylic acid;

(R)-1-(3-(5-Methyl-5,6-dihydrodibenz[b,e]azepin-11-ylidene)-1-propyl)-3-piperidinecarboxylic acid;

(R)-1-(3-(9H-Tribenzo[a,c,e]cyclohepten-9-ylidene)-1-propyl)-3-piperidinecarboxylic acid;

(R)-1-(3-(9H-Tribenzo[b,d,f]azepine-9-yl)propyl)-3-piperidinecarboxylic acid; or a pharmaceutically acceptable salt thereof.

15. A compound according to claim 1 which is:

1-(3-(9H-Tribenz[b,d,f]azepin-9-yl)-1-propyl)-3-piperidinecarboxylic acid;

1-(3-(Tribenzo[a,c,e]cyclohepten-9-ylidene)- 1-propyl)-3-piperidinecarboxylic acid;

1-(3-(6-Methyl-6H-dibenzo[c,f][1,2]thiazepin-5,5-dioxide-11-ylidene)-1-propyl)-3-piperidinecarboxylic acid;

1-(3-(10-Methyl-10,11-dihydro-dibenzo[b,e][1,4]diazepin-5-yl)-1-propyl)-3-piperidinecarboxylic acid; or a pharmaceutically acceptable salt thereof.

16. A pharmaceutical composition comprising a compound according to claim 1 together with a pharmaceutically acceptable carrier or diluent.

17. The pharmaceutical composition according to claim 16 wherein the compound is present in an amount between 0.5 mg and 1000 mg per unit dose.

18. A method of treating diabetic neuropathy, migraine, neurogenic inflammation, or rheumatoid arthritis in a subject in need of such treatment comprising administering to the subject an effective amount of a compound according to claim 1.

19. A method of treating insulin resistance in a subject in need of such treatment comprising administering to the subject an effective amount of a compound according to claim 1.

20. A method of treating diabetic neuropathy, migraine, neurogenic inflammation, or rheumatoid arthritis in a subject in need of such treatment comprising administering to the subject a pharmaceutical composition according to claim 16.

21. A method of treating insulin resistance in a subject in need of such treatment comprising administering to the subject a pharmaceutical composition according to claim 16.

* * * * *

UNITED STATES PATENT AND TRADEMARK OFFICE
CERTIFICATE OF CORRECTION

PATENT NO. : 5,753,643
DATED : May 19, 1998
INVENTOR(S) : Andersen et al.

It is certified that error appears in the above-identified patent and that said Letters Patent is hereby corrected as shown below:

On the Title page item [30], delete "Apr. 7, 1995 [DK] Denmark ..... 0406/96", and insert --Apr. 7, 1995 [DK] Denmark ..... 0406/95--

Signed and Sealed this

Twenty-sixth Day of September, 2000

Attest:

Q. TODD DICKINSON

*Attesting Officer*       *Director of Patents and Trademarks*